United States Patent [19]

Iwayama et al.

[11] 4,409,413

[45] Oct. 11, 1983

[54] CONVERSION OF XYLENES CONTAINING ETHYL BENZENE

[75] Inventors: Kazuyoshi Iwayama, Kamakura; Takehisa Inoue, Tokyo, both of Japan

[73] Assignee: Toray Industries, Incorporated, Tokyo, Japan

[21] Appl. No.: 274,318

[22] Filed: Jun. 16, 1981

[30] Foreign Application Priority Data

Jun. 23, 1980 [JP] Japan ............................ 55-83952
Oct. 9, 1980 [JP] Japan ............................ 55-140408

[51] Int. Cl.³ ..................... C07C 5/22; C07C 4/12
[52] U.S. Cl. ......................... 585/481; 585/488; 585/489
[58] Field of Search ........................ 585/481, 488

[56] References Cited

U.S. PATENT DOCUMENTS

| | | | |
|---|---|---|---|
| 3,632,835 | 1/1972 | Mitsche | 585/481 |
| 3,992,468 | 11/1976 | Cosyns et al. | 585/489 |
| 3,997,618 | 12/1976 | Cornely et al. | 585/481 |
| 4,105,706 | 8/1978 | Gallagher | 585/481 |

*Primary Examiner*—Curtis R. Davis
*Attorney, Agent, or Firm*—Scully, Scott, Murphy & Presser

[57] ABSTRACT

A mixture of xylene isomers containing ethyl benzene is contacted with a catalyst comprising a mordenite type zeolite and rhenium or phosphorus in the presence of hydrogen to isomerize xylenes and at the same time dealkylate ethyl benzene into mainly benzene.

6 Claims, No Drawings

CONVERSION OF XYLENES CONTAINING ETHYL BENZENE

BACKGROUND OF THE INVENTION

This invention relates to a process for the catalytic conversion of xylenes containing ethyl benzene. More particularly, it is concerned with a process wherein xylenes containing ethyl benzene are contacted with a specific catalyst in vapor phase and in the presence of hydrogen to isomerize xylenes and convert the ethyl benzene into other aromatic hydrocarbons.

Among the xylene isomers, it is para-xylene and ortho-xylene that are industrially important at present. Para-xylene as a raw material of polyester synthetic fibers has been in increasingly great demand, and this tendency will not be changed also in future. Ortho-xylene is utilized as a raw material of phthalic acid ester, a plasticizer of polyvinyl chloride, but the present demand for ortho-xylene is less than that for para-xylene. On the other hand, meta-xylene finds little industrial application at present. Under the circumstances, it is important from the industrial point of view to convert meta- and ortho-xylenes into para-xylene.

Xylene isomers are close to one another in their boiling points, particularly the boiling point of para-xylene and that of meta-xylene are extremely close to each other, so it is disadvantageous from the economic point of view to separate para-xylene from the other xylene isomers by the distillation processing, for which reason the industrial separation of para-xylene has so far been conducted by the low temperature processing which utilizes the difference in melting point. In the low temperature processing, due to eutectic point, there is a limit to the recovery of para-xylene per pass, which is at most 60% per pass; as a result, the raffinate after recovery of para-xylene exhibits a fairly high concentration of para-xylene. There has recently been developed adsorption processing as a new separation technique as described in Japanese Pat. Nos. 17246/74, 28181/74, 10547/75, 11343/75 and 46093/76. According to the absorption processing, theoretically, para-xylene can be recovered 100% per pass; that is, the concentration of para-xylene in the raffinate after its adsorptive separation is very low, which is zero theoretically.

Ortho-xylene, in general, has so far been separated by the precision distillation processing.

The raffinate after separation of para- and ortho-xylenes is transferred to the isomerization process, where meta-xylene and/or ortho-xylene is isomerized up to the para-xylene concentration close to the thermodynamic equilibrium composition, then mixed with a fresh feed stock and transferred to the separation process, and this cycle is repeated. In such a combined process, when feeding to the isomerization process the raffinate after separation of para-xylene by the low temperature processing, as mentioned above, the concentration of para-xylene in the raffinate is relatively high, while the raffinate after separation of para-xylene by the adsorption processing exhibits a very low concentration of para-xylene. Consequently, a greater severity is required of the latter in the reaction in the isomerization process.

In general, xylenes utilized industrially are reformate xylenes obtained by reforming of naphtha and by subsequent aromatic extraction and fractional distillation, or pyrolysis xylenes obtained by aromatic extraction and fractional distillation of cracked gasoline by-produced from thermal cracking of naphtha. Pyrolysis xylenes are particularly characteristic in that the concentration of ethyl benzene is higher by two times or more than that of reformate xylenes. Table 1 below shows typical compositions of both reformate and pyrolysis xylenes.

TABLE 1

| Component | Xylene Composition Reformate | Pyrolysis |
|---|---|---|
| Ethyl benzene | 18 wt. % | 39 wt. % |
| p-xylene | 19 | 13 |
| m-xylene | 42 | 32 |
| o-xylene | 21 | 16 |

Thus, in a mixture of xylene isomers there generally exist a fairly large amount of ethyl benzene, but unless ethyl benzene is removed by some means, it will become accumulated and its concentration will increase as the separation and isomerization processes are recycled, and thus the presence of ethyl benzene remaining unremoved results undesirably. For this reason, reformate xylenes containing less ethyl benzene are preferably utilized at present as a fresh feed stock. Anyhow, it is necessary to lower the concentration of ethyl benzene, and to this end there have been practised some methods industrially and some methods have been proposed. These methods are broadly classified into one involving direct separation of ethyl benzene and the other involving conversion by reaction of ethyl benzene into other useful compounds.

As the method of separating ethyl benzene, mention may be made of the distillation processing, and in this case it is necessary to carry out an ultra-precision distillation because of a small difference in boiling point between ethyl benzene and xylenes, whose industrial execution requires an enormous equipment investment and high running expenses, so the distillation processing is disadvantageous from the economic point of view.

Recently, as set forth in Japanese Patent Laid Open Publication No. 10223/77, etc., there has been proposed the adsorption processing for the separation of ethyl benzene, but its separation performance is not fully satisfactory.

As other means for removing ethyl benzene there have been proposed methods of converting it into other useful components, typical of which is the conversion of ethyl benzene into xylenes as is described in Japanese Pat. Nos. 46606/74, 47733/74, 15044/76, 36253/76 and Japanese Patent Laid Open Publication No. 16390/79. In this method, however, it is essential that platinum, a very expensive noble metal, be contained in the catalyst used.

In the conversion of ethyl benzene to xylenes, moreover, it is necessary from the standpoint of reaction mechanism that non-aromatic components such as naphthenes and paraffins be present therein, with their concentrations in the product reaching several percent to ten-odd percent. Furthermore, there is a limit to the conversion of ethyl benzene since it is restricted by thermodynamic equilibrium (see Table 2).

TABLE 2

| Equilibrium composition of xylene isomers (%) | | | |
|---|---|---|---|
| Temperature (°K.) | 600 | 800 | 1000 |
| Ethyl benzene | 5.9 | 10.8 | 15.5 |
| p-xylene | 22.4 | 20.6 | 19.0 |
| m-xylene | 50.1 | 45.8 | 42.3 |

TABLE 2-continued

| Equilibrium composition of xylene isomers (%) | | | |
| --- | --- | --- | --- |
| Temperature (°K.) | 600 | 800 | 1000 |
| o-xylene | 21.6 | 22.8 | 23.2 |

A method of converting ethyl benzene into other components than xylenes has recently been proposed in Japanese Pat. No. 41657/78 and Japanese Patent Laid Open Publication No. 148028/77. According to this method, simultaneously with the isomerization of xylenes, ethyl benzene is converted to benzene and diethylbenzene by disproportionation reaction and by utilization of their great difference in boiling point from xylenes it is intended to separate them. The benzene thus obtained is in great demand as a raw material of the synthetic fiber nylon, but there is little demand for the diethylbenzene, which is necessary to be further converted into some other useful compound though this additional operation results in disadvantage economically. In addition, since the disproportionation reaction of ethyl benzene is restricted by thermodynamic equilibrium, there is a limit to the conversion of ethyl benzene.

In view of the above circumstances, it is keenly desired at present to provide a method capable of converting ethyl benzene into a useful compound without being restricted by thermodynamic equilibrium. Furthermore, as will be apparent from what has been mentioned hereinbefore, there exists a keen demand for the development of a catalyst system having characteristics permitting an effective use of even xylenes having a high concentration of ethyl benzene, e.g. pyrolysis xylenes, and, in the isomerization of xylenes, capable of sufficiently isomerizing even raffinate after adsorptive separation of para-xylene.

In view of such present situations, we have considered, for the removal of ethyl benzene, a catalyst system permitting the hydrodealkylation of ethyl benzene into benzene under little influence of thermodynamic restrictions and ethane and the simultaneous isomerization of xylenes; as a result, having reached the conclusion that this reaction can be performed by combination of a solid acid component and a hydrogenation component, we made extensive studies about various catalysts.

SUMMARY OF THE INVENTION

It is an object of this invention to provide a conversion process for xylenes containing ethyl benzene.

It is another object of this invention to provide a process for the hydrodealkylation of ethyl benzene simultaneously with the isomerization of xylenes.

Other objects and advantages of this invention will become apparent from the following description.

The aforesaid objects of this invention can be achieved by contacting xylenes containing ethyl benzene with a catalyst comprising a mordenite type zeolite and rhenium and/or phosphorus, in the presence of hydrogen.

The incorporation of rhenium component and/or phosphorus component in the above catalyst suppresses the disproportionation between xylenes or the transalkylation between xylenes and ethyl benzene, and allows the dealkylation of ethyl benzene to benzene to proceed more efficiently.

If at least one member selected from the group consisting of molybdenum, tungsten and vanadium is added to the above catalyst, the catalyst activity will be further improved.

DETAILED DESCRIPTION OF THE INVENTION

Both synthetic and natural mordenite type zeolites may be used in the invention, and mixtures thereof are also employable, of course.

Mordenite type zeolites, as known well, belong to a crystalline aluminosilicate composed of silica and alumina, the aluminosilicate consisting basically of a three-dimensional framework wherein tetrahedra of $SiO_4$ and $AlO_4$ are cross-linked sharing oxygen atoms. The aluminum-containing tetrahedra bear a negative charge and maintain its electrical neutralization by containing alkali metal ion, alkaline earth metal ion, or other cations. These cations are exchangeable with other cations by the known ion-exchange technique.

Generally, synthetic mordenite type zeolites contain mainly sodium ions, while natural ones contain mainly various alkali metal ions and/or alkaline earth metal ions. Among these metal ions, it is calcium ion that is particularly preferred in this invention. It is more preferable that mordenite type zeolites containing sodium ion by ion-exchanged with calcium ion. But mordenite type zeolites not containing calcium ion are also employable in the invenion, of course.

It is necessary that mordenite type zeolites when used in the invention should be endowed with acidity by being subjected to dealkalization treatment. The dealkalization treatment as referred to herein is a kind of ion-exchange treatment wherein a zeolite is treated with a solution containing an acid and/or an ammonium salt compound to introduce therein hydrogen ion or ammonium ion as a hydrogen ion precursor.

The dealkalization treatment is generally conducted using an aqueous solution of an acid or an ammonium compound. Both inorganic and organic acids may be used. Examples of inorganic acids are hydrochloric, nitric, phosphoric and carbonic acids, but other acids are also employable provided they should contain hydrogen ion. Examples of organic acids are formic, acetic, propionic, oxalic, citric and tartaric acids. Too high concentrations of inorganic acids are not desirable because the treatment with their solutions would result in the treated mordenite structure being destroyed. Preferred concentrations of acids greatly vary according to the kind of acids used, so it is difficult to absolutely define such concentrations, but ample care should be exercised to avoid destruction of the mordenite structure.

As the ammonium salt compound there may be used, for example, inorganic ammonium salts such as ammonium nitrate, ammonium chloride, ammonium sulfate, ammonium carbonate and aqueous ammonia, and organic ammonium salts such as ammonium formate, ammonium acetate and ammonium citrate, of which inorganic ammonium salts are preferred. Ammonium salts are used as a solution of preferably from 0.05 N to 4 N, more preferably from about 0.1 N to 2 N. Both batch method and flow method are preferred for the dealkalization of mordenite type zeolites with a solution of an acid and/or an ammonium salt. In case the treatment is made by the batch method, the solid-liquid ratio should be at least the amount permitting a sufficient contact of zeolite with liquid, preferably about 1 l/kg or more. A treatment time from about 0.1 to 72 hours is sufficient, preferably from about 0.5 to 24 hours, and a treatment temperature below the boiling point is sufficient, but preferably heat is applied to accelerate the dealkalization. It is sufficient to apply the treatment once, but if required the treatment may be repeated.

In case the treatment is made by the flow method, there may be adopted the fixed-bed process and the fluidized-bed process, but some consideration is needed to avoid the occurrence of fluid channelling or of non-uniform dealkalization.

If there is applied the foregoing calcium ion exchange treatment, it may be carried out either simultaneously with or prior to the dealkalization treatment.

Generally, the calcium ion exchange treatment is performed in an aqueous solution. Inorganic salts, e.g. nitrates, sulfates and chlorides, are preferred as calcium ions. The concentration of calcium ions in the ion-exchange solution is preferably from about 0.05 to 4 N and more preferably from about 0.1 to 2 N. Both batch method and flow method are preferable for the ion exchange. In the case of adopting the batch method, the solid-liquid ratio should be at least the amount permitting a sufficient contact of zeolite with liquid, preferably about 1 l/kg or more. It is sufficient to perform the treatment for a period of time ranging from about 0.1 to 72 hours, more preferably from about 0.5 to 24 hours. Temperatures below the boiling point are sufficient, but preferably heat is applied to accelerate the ion exchange treatment. The number of time of this treatment to be applied is once or more, preferably several times repeated, although it also depends on the concentration of calcium ions in the ion-exchange solution. In case the flow method is to be followed, there may be adopted the fixed-bed process and the fluidized-bed process as is the case with the dealkalization treatment. But in the case of the flow method, some consideration is needed particularly to avoid the occurrence of fluid channelling or so that ion exchange may become uniform. The calcium ion exchange treatment is followed by washing with water. For the aqueous solution there preferably is used a distilled water, and the water-washing may be done according to either the batch method or the flow method.

The mordenite zeolite after subjected to the dealkalization treatment is then washed with water, preferably in distilled water, which may be performed according to either the batch method or the flow method. In this way, hydrogen ion or ammonium ion is introduced in the mordenite type zeolite. As the dealkalization treatment proceeds, the catalytic activity increases to a large extent, but at the same time there occur side reactions, therefore, an excessive dealkalization treatment is not desirable. A particularly preferred dealkalization percentage is from 20% to 50%, that is, 0.2 to 0.5 equivalent of hydrogen ion or hydrogen ion precursor such as ammonium ion per gram-atom aluminum of a mordenite type zeolite. In other words, it is desirable that exchangeable metal ions be present in an amount of 0.5 to 0.8 equivalent per gram-atom aluminum. At a dealkalization percentage less than 20%, there is little catalytic activity, which is substantially inert.

The mordenite type zeolite thus subjected to the dealkalization treatment is dried and, if required, calcined. The drying is performed for over 0.1 hour, preferably from 0.5 to 48 hours, at a temperature of 50° to 250° C., preferably from 100° to 200° C. And the calcination is performed preferably for over 1 hour at a temperature of 300° to 700° C. and more preferably for 0.5 to 24 hours at a temperature of 400° to 600° C.

The dealkalization treatment may be done either before or after supporting the rhenium or phosphorus component on the mordenite, but the former is preferred.

As the rhenium component there may be used such rhenium compounds as rhenium oxide, sulfide and selenide, or the rhenium element.

For supporting rhenium on the mordenite type zeolite there may be adopted, preferably, kneading method, impregnating method, and a physical mixing of powders with each other, but the supporting method is not always limited to these methods, provided a more uniform dispersion of the rhenium component in the mordenite type zeolite is preferred for higher activity and selectivity and for this reason the kneading method and the impregnating method are preferred and the former is particularly preferred. According to the kneading method, the mordenite component is pulverized into a powder of below 100 mesh and this powder is kneaded with the rhenium component sufficiently homogeneously in the presence of water. Such a sufficiently homogeneous kneading requires a kneading time over 10 minutes, preferably over 30 minutes. In the case of the impregnating method, soluble perrhenium acid or ammonium perrhenate is used preferably since the mordenite component is contacted with an aqueous containing the rhenium component.

The amount of a rhenium compound to be supported is 0.01% to 3%, preferably 0.05% to 0.5%, by weight in terms of the rhenium element based on the total weight. Rhenium (VII) oxide as a rhenium component supported on the mordenite type zeolite easily dissolves in water as perrhenium acid, so rhenium (VII) oxide in its supported state may be contacted with hydrogen sulfide to form insoluble rhenium sulfide.

The addition of phosphorus to the mordenite type zeolite may be carried out in the same manner as in the addition of rhenium component thereto, but particularly the kneading method is preferred.

As the phosphorus component there usually are employed phosphorus compounds such as, for example, phosphoric acid, ammonium dihydrogenphosphate, diammonium hydrogenphosphate, ammonium phosphate, aluminium hydrogenphosphate, aluminium phosphate, ammonium phosphomolybdate, ammonium phosphorus walframate, and copper phosphate. The amount of phosphorus to be added is from 0.1% to 20%, preferably from 1% to 10%, by weight as the phosphorus element based on the total catalyst weight. The total catalyst weight as referred to herein means the weight of catalyst in a state not containing moisture. A too small amount of phosphorus would be ineffective, while a too large amount thereof would result in coverage of the active center of zeolite which reduces activity remarkably, so these amounts are not desirable.

The addition of molybdenum, tungsten or vanadium to the mordenite type zeolite may be made in the same manner as in the addition of rhenium or phosphorus thereto.

As the molybdenum component there may be used, for example, ammonium molybdate, ammonium phosphomolybdate, molybdic acid, molybdenum oxide, molybdenum sulfide, and molybdates. Examples of the tungsten component are ammonium tungstate, ammonium phosphorus wolframate, tungsten oxide, tungsten sulfide, tungsten carbide, and tungstates. And examples of the vanadium component are ammonium metavanadate, vanadium oxynitrate, vanadium oxysulfate, vanadium oxyoxalate, vanadium oxydichloride, vanadium oxide, and vanadates. These components may be used alone or as a mixture of two or more. The amount of molybdenum, tungsten, or vanadium to be added is from 0.1% to 10%, preferably from 0.2% to 5%, by weight as the element. A too small amount would be ineffective, while a too large amount would cause side reaction, so both excessively small and large amounts are not desirable.

Either a fixed bed or a fluidized bed may be used as a reaction apparatus in this invention, but the former is preferred because of simpler construction and easier operation. In the fixed bed process, it is preferable in view of the catalyst effective factor that the catalyst particle diameter be as small as possible, provided a too small particle diameter is not desirable because it would cause an increase in pressure loss. That is, there exists a preferable range of catalyst particle diameter, which is from 0.05 to 10 mm, more preferably from 0.1 to 2 mm. As the case may be, molding is needed in order to obtain a catalyst having such a preferred range of particle diameter, for example, compression molding and extrusion. And in order to improve the moldability of impart strength to the catalyst, there may be used a binder, though it goes without saying that the use of a binder may be omitted if molding is attainable to a satisfactory extent without the binder. As the binder there are preferably used clays such as bentonite and terra alba, or silicasol and aluminasol. The amount of the binder to be added is below 30%, preferably below 20%, by weight based on the total catalyst weight. The molding may be done either before or after the dealkalization treatment of mordenite type zeolite, or it may be performed even before or after the addition or rhenium or phosphorus. In short, the molding may be done according to the easiest feasible method in consideration of the shape of mordenite type zeolite used, the kind of rhenium compound, phosphorus compound, etc. and further the method of their addition.

The catalyst thus prepared is dried subsequently calcined before its use. The drying is performed for over 0.1 hour, preferably 0.5 to 48 hours, at a temperature of 50° to 250° C., preferably 100° to 200° C., and the calcination is conducted for over 0.1 hour at a temperature of 300° to 700° C., preferably for 0.5 to 24 hours at 400° to 600° C.

By such a calcination the ammonium ions introduced in the mordenite type zeolite by the dealkalization treatment are converted to hydrogen ions, which in turn are converted to decation type as the calcination temperature increases, and the catalyst in such a form is also employable effectively, of course.

The catalyst prepared in the manner mentioned above is used under the following reaction conditions. That is, the operating temperature ranges from 300° to 600° C., preferably from 350° to 550° C., the operating pressure ranges from atmospheric pressure to 100 kg/cm$^2$·G, preferably from atmospheric pressure to 50 kg/cm$^2$·G, and the time factor W/F (g-cat·hr/g-mol feed stock)(W: catalyst weight, F: mol feed stock per hour) which means the contact time of reaction is 1 to 200, preferably 5 to 150. In the reaction system there should be present hydrogen, which is necessary for the dealkylation of ethyl benzene. If the hydrogen concentration is too low, the dealkylation reaction of ethyl benzene will not proceed sufficiently and carbonaceous compounds will be deposited on the catalyst resulting in deterioration of the catalyst activity. A too high concentration of hydrogen is not desirable, either, because it would cause an increase of hydrocracking reaction. There exists a preferable range of hydrogen concentration, which is 1 to 50, preferably 3 to 30, in terms of mol ratio of hydrogen to feed stock ($H_2$/F).

As the feed stock there is used a mixture of xylene isomers containing ethyl benzene, wherein the concentration of ethyl benzene is not particularly limited. The concentration of para-xylene in the mixture of xylene isomers is preferably below the thermodynamic equilibrium concentration, but it is of course possible, as one mode of use in this invention, to use as the feed stock a mixture of xylene isomers containing para-xylene of the thermodynamic equilibrium concentration with a view to decreasing the concentration of ethyl benzene.

The feed stock may contain other aromatic components, e.g. benzene, toluene, tri-methylbenzene, ethyltoluene, diethylbenzene, ethylxylene, provided their concentrations should be in a low range.

The invention is further illustrated by the following examples.

EXAMPLE 1 AND COMPARATIVE EXAMPLE 1

"Zeolon 100-NA" powder, a synthetic mordenite manufactured by Norton Company, was subjected to an ion-exchange treatment with a 0.187 N aqueous ammonium chloride solution at a solid-liquid ratio of 5 (l/kg) by heating to 80°–90° C. for 30 minutes according to the batch method, followed by washing thoroughly with distilled water and drying overnight at 110° C. This ion-exchanged "Zeolon 100-NA" powder was extracted with nitric acid to determine the sodium content by flame analysis; as a result, the dealkalization percentage was found to be 36.4%. To this mordenite powder was added aluminsol as a binder in an amount of 15% by weight in terms of alumina ($Al_2O_3$), and then an aqueous perrhenium acid solution was added in an amount of 0.1% by weight in terms of rhenium (Re), followed by kneading and molding. The molded particles were classified to 10–24 mesh (JIS sieve), then dried overnight at 110° C. and subsequently calcined at 500° C. for 2 hours. The catalyst thus prepared will be referred to hereinafter simply as the catalyst "A". On the other hand, as a comparative example, there was prepared a catalyst in the same way as above except that perrhenium acid was not added, which catalyst will be referred to hereinafter as the catalyst "B".

To the catalysts "A" and "B" there was fed ethyl benzene alone. As a result, there were obtained such results as set out in Table 3 below.

TABLE 3

| | Item Catalyst | Example 1 A | Comparative Example 1 B |
|---|---|---|---|
| Reaction Conditions | Reaction temperature (°C.) | 450 | 450 |
| | Reaction pressure (kg/cm$^2$ · G) | 15.3 | 15.3 |
| | H$_2$/F (mol/mol) | 18 | 18 |
| | W/F | 70 | 70 |
| | Reaction time (HR) | 5 | 5 |
| Reaction Products | BZ wt. % | 54.1 | 12.5 |
| | C$_8$NP | 0.1 | 0.0 |
| | TOL | 2.3 | 0.2 |
| | ET | 0.3 | 0.3 |
| | DEB | 2.0 | 11.6 |
| EB conversion % | | 64.7 | 27.7 |
| R.L. | | 0.0 | 0.8 |

Reference to the above table shows that the catalyst "A", as compared with the catalyst "B", affords a high conversion of ethyl benzene and a remarkable improvement in selective dealkylation.

EXAMPLE 2 AND COMPARATIVE EXAMPLES 2 AND 3

"Zeolon 100-NA" powder, a synthetic mordenite manufactured by Norton Company, was subjected to an ion-exchange treatment with a 0.281 N aqueous ammonium chloride solution at a solid-liquid ratio of 5 (l/kg) by heating to 80°–90° C. for 30 minutes according to the batch method, followed by thorough washing with distilled water and drying overnight at 110° C. The dealkalization percentage of this ion-exchanged "Zeolon 100-NA" was 43.5%.

To this mordenite powder was added aluminasol as a binder in an amount of 15% by weight in terms of alumina ($Al_2O_3$), and then an aqueous perrhenium acid solution was added in an amount of 0.1% by weight in terms of rhenium (Re), followed by kneading for about 1 hour and subsequent extrusion. The molded particles were classified to 10–24 mesh, then dried overnight at 110° C. and calcined at 500° C. for 2 hours. The catalyst thus prepared will be referred to hereinafter as the catalyst "C".

On the other hand, there were prepared a catalyst using, in place of perrhenium acid, an aqueous chloroplatinic acid solution in an amount corresponding to 0.05% by weight of platinum which catalyst will be referred to hereinafter as the catalyst "D", and a catalyst using an aqueous nickel nitrate solution in an amount corresponding to 0.2% by weight of nickel which catalyst will be referred to hereinafter as the catalyst "E".

To the catalysts "C", "D" and "E" there was fed ethyl benzene. The results of the reaction are set out in Table 4, from which it is seen that rhenium, as compared with platinum and nicketl, contributes more to the improvement of selectivity in the dealkylation of ethyl benzene to benzene.

TABLE 4

| | | Example 2 | Comparative Example 2 | Comparative Example 3 |
|---|---|---|---|---|
| | Item | | | |
| | Catalyst | C | D*1 | E |
| | Supported Metal | Re | Pt | Ni |
| Reaction Conditions | Reaction temperature (°C.) | 400 | 400 | 400 |
| | Reaction pressure ($kg/cm^2 \cdot G$) | 15.3 | 15.3 | 15.3 |
| | $H_2/G$ (mol/mol) | 18 | 18 | 18 |
| | W/F (g-cat · hr/g-mol) | 35 | 35 | 35 |
| | Reaction time (HR) | 5 | 5 | 5 |
| Reaction products | BZ wt. % | 13.6 | 2.2 | 4.6 |
| | $C_8NP$ | 0.1 | 31.7 | 0.4 |
| | TOL | 0.8 | 0.4 | 0.1 |
| | ET | 0.3 | 0.4 | 0.1 |
| | DEB | 5.1 | 1.8 | 4.5 |
| EB conversion (wt. %) | | 25.5 | 56.8 | 11.2 |
| R.L. | | 2.0 | 4.3 | 0.7 |

*1 18.2% of xylene was produced.

EXAMPLES 3, 4 AND 5

"Zeolon 100-NA" powder, a synthetic mordenite manufactured by Norton Company, was ion-exchanged with a 0.131 N aqueous ammonium chloride solution in the same manner as in Example 1, then washed with water and dried. The dealkalization percentage of this mordenite powder was 27.3%. To this powder was added aluminasol as a binder in an amount of 15% by weight in terms of alumina ($Al_2O_3$), and then an aqueous perrhenium acid solution was added in an amount of 0.1% by weight as rhenium (Re), followed by kneading and molding. The molded catalyst will be referred to hereinafter as the catalyst "F".

In the same manner "Zeolon 100-NA" powder was ion-exchanged with a 0.374 N aqueous ammonium chloride solution, followed by water-washing and drying. The dealkalization percentage of this mordenite powder was 60.0%. To this powder was added aluminasol as a binder in an amount of 15% by weight in terms of alumina ($Al_2O_3$), and then an aqueous perrhenium acid solution was added in an amount of 0.1% by weight as rhenium (Re), followed by kneading and molding to give a molded catalyst, which catalyst will be referred to hereinafter as the catalyst "G".

To the catalyst "A" prepared in Example 1 and the catalysts "F" and "G" was fed as a feed stock a mixture of xylene isomers containing ethyl benzene. The results of the reaction are set out in Table 5.

EXAMPLE 6

Natural mordenite obtained in Miyagi Prefecture was crushed and then pulverized into a powder of below 200 mesh, which was then subjected to an ion-exchange treatment with a 0.281 N aqueous ammonium chloride solution at a solid-liquid ratio of 5 (l/kg) by heating to 80°–90° C. for 1 hour according to the batch method. The dealkalization percentage of this powder was 39.0%. The powder was then thoroughly washed with distilled water and dried overnight at 110° C. To this ion-exchanged natural mordenite was added aluminasol in an amount of 3% by weight in terms of alumina ($Al_2O_3$), and to the resulting mixture was added an aqueous perrhenium acid solution in an amount of 0.2% by weight as rhenium (Re), followed by kneading and molding. Then, after classifying to 10–24 mesh, the particles were dried overnight at 110° C. and subsequently calcined at 500° C. for 2 hours. The catalyst thus prepared will be referred to hereinafter as the catalyst "H". A mixture of xylene isomers containing ethyl benzene as a feed stock was allowed to react, the results of which are shown in Table 5.

TABLE 5

| | Item | Example 3 | Example 4 | Example 5 | Example 6 |
|---|---|---|---|---|---|
| | Catalyst | A | F | G | H |
| Reaction Conditions | Reaction temperature (°C.) | 450 | 450 | 450 | 450 |
| | Reaction pressure ($kg/cm^2 \cdot G$) | 5.0 | 5.0 | 5.0 | 5.0 |

TABLE 5-continued

| Item | | Example 3 | Example 4 | Example 5 | Example 6 |
|---|---|---|---|---|---|
| Catalyst | | A | F | G | H |
| H$_2$/F (mol/mol) | | 6.0 | 6.0 | 6.0 | 6.0 |
| W/F (g-cat · hr/g-mol) | | 70 | 88 | 35 | 35 |
| Reaction time (HR) | | 5 | 5 | 5 | 5 |
| | Feed stock | | | | |
| Reaction Products | C$_7^-$ wt. % | 0.0 | 2.0 | 2.1 | 2.9 | 1.6 |
| | BZ | 0.0 | 4.6 | 3.4 | 6.5 | 3.0 |
| | C$_8$NP | 0.0 | 0.0 | 0.0 | 0.0 | 0.0 |
| | TOL | 0.1 | 4.6 | 3.7 | 10.5 | 3.9 |
| | EB | 24.9 | 15.7 | 17.9 | 10.5 | 18.7 |
| | PX | 0.3 | 16.2 | 16.6 | 13.9 | 16.7 |
| | MX | 74.2 | 35.9 | 37.3 | 30.8 | 37.2 |
| | OX | 0.5 | 15.9 | 16.5 | 13.6 | 16.5 |
| | ET | 0.0 | 1.2 | 0.6 | 2.6 | 0.5 |
| | TMB | 0.0 | 2.3 | 1.2 | 6.2 | 1.1 |
| | DEB | 0.0 | 0.7 | 0.5 | 0.8 | 0.5 |
| | EX | 0.0 | 1.1 | 0.4 | 1.8 | 0.3 |
| EB conversion % | | | 36.9 | 28.1 | 57.8 | 24.9 |
| PX/XY | | | 23.8 | 23.6 | 23.8 | 23.7 |
| XY recovery | | | 90.7 | 93.9 | 77.7 | 93.9 |

EXAMPLE 7

"Zeolon 100-NA" powder, a sodium type mordenite manufactured by Norton Company, was subjected to an ion-exchange treatment with a 0.197 N aqueous ammonium chloride solution at a solid-liquid ratio of 5 (l/kg) by heating to 80°–90° C. for 30 minutes according to the batch method, followed by thorough washing with distilled water and drying overnight at 110° C. The dealkalized "Zeolon 100-NA" powder was extracted with nitric acid to determine the sodium content by flame analysis; as a result, the dealkalization percentage was found to be 36.4%. To this mordenite powder were added aluminasol as a binder in an amount of 15% by weight in terms of alumina (Al$_2$O$_3$) and phosphoric acid in an amount of 5% by weight as phosphorus (P). The mixture was thoroughly kneaded and then molded into particles of 10–24 mesh (JIS sieve), followed by drying overnight at 110° C. and subsequent calcination at 500° C. for 2 hours in the presence of air. The catalyst thus prepared will be referred to hereinafter as the catalyst "I". The catalyst "I" was checked for activity, the results of which are shown in Table 6.

EXAMPLE 8

"Zeolon 100-NA" powder, a sodium type synthetic mordenite manufactured by Norton Company, was subjected to an ion-exchange treatment with a 0.169 N aqueous calcium nitrate solution at a solid-liquid ratio of 5 (l/kg) by heating to 80°–90° C. for 30 minutes according to the batch method. Then, the powder was washed once with distilled water and again subjected to the calcium ion exchange treatment, and this operation was repeated five times, followed by thorough washing with distilled water and dried overnight at 110° C. The calcium exchange rate of this calcium ion exchanged "Zeolon 100-NA" was found to be 97.3% by flame analysis. This calcium type mordenite powder was then subjected to a dealkalization treatment with a 0.187 N aqueous ammonium chloride solution at a solid-liquid ratio of 5 (l/kg) by heating to 80°–90° C. for 30 minutes according to the batch method, followed by thorough washing with distilled water and drying overnight at 110° C. The dealkalization percentage of this calcium type mordenite was 32.1%. To this mordenite powder were added aluminasol in an amount of 15% by weight in terms of alumina (Al$_2$O$_3$), phosphoric acid in an amount of 5% by weight as phosphorus (P) and an aqueous perrhenium acid solution in an amount of 0.1% by weight as rhenium (Re). After kneading, the mixture was molded to 10–24 mesh, then dried overnight at 110° C. and calcined at 500° C. for 2 hours. The catalyst thus prepared will be referred to hereinafter as the catalyst "J". The catalyst "J" was checked for activity, the results of which are shown in Table 6.

EXAMPLES 9, 10 AND 11

In the same manner as in Example 8 "Zeolon 100-NA" was subjected to the calcium ion exchange treatment and the subsequent dealkalization treatment. To the so-treated "Zeolon 100-NA" powder were added aluminasol as a binder in an amount of 15% by weight in terms of alumina (Al$_2$O$_3$), phosphoric acid in an amount of 5% by weight as phosphorus (P) and an aqueous ammonium molybdate solution in an amount of 1% by weight as molybdenum (Mo), followed by kneading thoroughly. Then, the mixture was molded into 10–25 mesh particles, dried overnight at 110° C. and thereafter calcined in air at 500° C. for 2 hours. The catalyst thus prepared will be referred to hereinafter as the catalyst "K".

On the other hand, a catalyst was prepared in the same manner as above by adding to the dealkalized calcium type mordenite powder phosphoric acid in an amount of 5% by weight as phosphorus (P), an aqueous ammonium tungstate solution in an amount of 1% by weight as tungsten (W) and aluminasol as a binder. This catalyst will be referred to hereinafter as the catalyst "L".

Also, a catalyst was prepared in the same way as above by adding to the dealkalized calcium type mordenite powder phosphoric acid in an amount of 5% by weight, an aqueous perrhenium acid solution in an amount of 0.1% by weight as rhenium (Re), an aqueous ammonium metavanadate in an amount of 1% by weight as vanadium (V) and aluminasol as a binder. This catalyst will be referred to hereinafter as the catalyst "M".

The catalysts "K", "L" and "M" were checked for activity, the results of which are shown in Table 6.

TABLE 6

| Item Catalyst | | Ex. 7 I | Ex. 8 J | Ex. 9 K | Ex. 10 L | Ex. 11 M |
|---|---|---|---|---|---|---|
| Reaction Conditions | Reaction temperature (°C.) | 450 | 450 | 450 | 450 | 450 |
| | Reaction pressure (kg/cm$^2$ · G) | 5.0 | 10.1 | 10.1 | 10.1 | 10.1 |
| | H$_2$/F (mol/mol) | 6.0 | 12.0 | 12.0 | 12.0 | 12.0 |
| | W/F (g-cat · hr/g-mol) | 35 | 70 | 35 | 35 | 35 |
| | Reaction time (HR) | 5 | 5 | 5 | 5 | 5 |
| | Feed Stock | | | | | |
| Reaction Products | C$_7^-$ wt. % | 0.0 | 0.8 | 1.6 | 1.3 | 1.2 | 1.6 |
| | BZ | 0.0 | 3.0 | 3.3 | 2.6 | 3.1 | 3.4 |
| | C$_8$NP | 0.0 | 0.0 | 0.0 | 0.0 | 0.0 | 0.0 |
| | TOL | 0.1 | 2.3 | 1.6 | 1.3 | 1.5 | 1.9 |
| | EB | 24.7 | 18.8 | 18.4 | 19.8 | 19.2 | 18.4 |
| | PX | 0.3 | 16.8 | 17.3 | 17.4 | 17.3 | 17.2 |
| | MX | 74.3 | 37.2 | 38.1 | 38.5 | 38.1 | 37.9 |
| | OX | 0.6 | 16.5 | 16.9 | 17.1 | 16.9 | 16.8 |
| | ET | 0.0 | 0.9 | 0.5 | 0.4 | 0.5 | 0.6 |
| | TMB | 0.0 | 1.3 | 1.0 | 0.7 | 0.9 | 1.1 |
| | DEB | 0.0 | 0.9 | 0.5 | 0.4 | 0.5 | 0.5 |
| | EX | 0.0 | 1.6 | 0.8 | 0.5 | 0.9 | 0.7 |
| EB conversion wt. % | | | 23.9 | 25.5 | 19.7 | 22.3 | 25.5 |
| PX/XY | | | 23.8 | 23.9 | 23.8 | 23.8 | 23.8 |
| XY recovery | | | 93.8 | 96.1 | 97.1 | 96.1 | 95.6 |

Note
C$_7^-$: non-aromatic components of C$_1$-C$_7$
BZ: benzene
C$_8$NP: C$_8$ naphthene, paraffin
TOL: toluene
EB: ethyl benzene
PX: para-xylene
MX: meta-xylene
OX: ortho-xylene
XY: xylenes
ET: ethyltoluene
TMB: trimethylbenzene
DEB: diethylbenzene
EX: ethylxylene
R.L.: ring loss (loss of benzene ring)

What is claimed is:

1. A process for simultaneously isomerizing xylenes and hydrodealkylating ethyl benzene to benzene by contacting a mixture containing ethyl benzene and at least one xylene isomer with a catalyst in the presence of hydrogen, said catalyst comprising a mordenite type zeolite which has been ion-exchanged with hydrogen ion and/or hydrogen ion precursor rhenium and phosphorus.

2. A process according to claim 1 wherein said mordenite type zeolite contains not more than 0.5 equivalent, per gram-atom of aluminum, of hydrogen ion and/or hydrogen ion precursor.

3. A process according to claim 1 wherein the reaction is carried out in vapor phase at a temperature in the range of from 300° to 600° C.

4. A process for simultaneously isomerizing xylenes and hydrodealkylating ethyl benzene to benzene by contacting a mixture containing ethyl benzene and at least one xylene isomer with a catalyst in the presence of hydrogen, said catalyst comprising a mordenite type zeolite which has been ion-exchanged with hydrogen ion and/or hydrogen ion precursor, phosphorus and vanadium.

5. A process according to claim 4 wherein said mordenite type zeolite contains not more than 0.5 equivalent, per gram-atom of aluminum, of hydrogen ion and/or hydrogen ion precursor.

6. A process according to claim 4 wherein the reaction is carried out in vapor phase at a temperature in the range of from 300° to 600° C.

* * * * *